United States Patent [19]
Marhold et al.

[11] Patent Number: 5,504,214
[45] Date of Patent: Apr. 2, 1996

[54] FLUORINATED BENZOTRIAZOLES

[75] Inventors: Albrecht Marhold, Leverkusen; Bernd Baasner, Bergisch Gladbach; Gerd Hänssler, Leverkusen, all of Germany

[73] Assignee: Bayer Aktiengesellschaft, Leverkusen, Germany

[21] Appl. No.: 184,887

[22] Filed: Jan. 21, 1994

[30] Foreign Application Priority Data

Jan. 29, 1993 [DE] Germany .................... 43 02 461.0

[51] Int. Cl.$^6$ ............................................. C07D 249/18
[52] U.S. Cl. ..................................... 548/259; 548/257
[58] Field of Search ................................. 548/257, 259

[56] References Cited

U.S. PATENT DOCUMENTS

| | | | |
|---|---|---|---|
| 2,806,035 | 9/1957 | Margot et al. | 548/259 |
| 4,240,822 | 12/1980 | Diehl et al. | 548/259 |
| 4,424,360 | 1/1984 | Hagedorn et al. | 548/257 |
| 4,609,394 | 9/1986 | Clark et al. | 71/90 |
| 4,788,292 | 11/1988 | Clark et al. | 548/257 |

FOREIGN PATENT DOCUMENTS

| | | |
|---|---|---|
| 0108908 | 5/1984 | European Pat. Off. . |
| 01787089 | 4/1986 | European Pat. Off. . |
| 0355049 | 2/1990 | European Pat. Off. . |
| 0367242 | 5/1990 | European Pat. Off. . |

OTHER PUBLICATIONS

Chemical Abstracts, vol. 60, No. 2, Jan. 20, 1964; CA#1732d: "Synthesis of 5-methyl-6-trifluoromethylbenzimidazole", J. Arient at al.
Chemical Abstracts, vol. 73, 1970, p. 358; CA#87890u: "Riboflavine analogs . . . ", G. A. Vavilov et al.
Chemical Abstracts, vol. 119, 1993, p. 934; CA#203733q: "Synthesis of acyclic analogs of benzotriazole and . . . ", B. G. Huang et al.
Agricultural Chemistry, p. 7, JP(A)–C, Week 9022, ICIL C03, 90–052796/08; "New herbicidal substda.–benzotriazole . . . ", Imperial Chem Inds, Apr. 24, 1990.
Agricultural Chemistry, Week 9036, AMCY C02, 90–141219/19; "Pyridyl: or phenyl:oxy–benzotriazole derivs . . . ", American Cyanamid, Jul. 27, 1990.
Agricultural Chemistry, p. 2, vol. 93, No. 7, JP(B)–C; J9 3012348–B, "Fungicidal N–aklyl– and N–alkenyl– . . . ", Celamerck GmbH, 2 pages. (1993).
Chemical Abstract. vol. 79, 1973, p. 360; 115594v: "1,2, 3–Benzotriazoles", H. Kitano et al.

*Primary Examiner*—Patricia L. Morris

[57] ABSTRACT

Substituted benzotriazoles, which contain at least 2 fluorine atoms per molecule, are excellent intermediates for preparing active compounds for pharmaceuticals and plant-protection agents; however, they themselves also exhibit a fungicidal effect.

4 Claims, No Drawings

FLUORINATED BENZOTRIAZOLES

The invention relates to benzotriazoles which contain at least 2 fluorine atoms per molecule and correspond to the

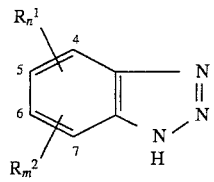
(I)

in which n and m=1 or 2,

R[1] represents $C_1-C_4$-fluoroalkyl, fluoro-$C_1-C_6$-alkoxy, fluoro-$C_1C_6$-alkylthio, fluoro-$C_1-C_6$-sulphonyl, substituted $C_6-C_{12}$-phenyl or substituted $C_6-C_{12}$-phenoxy, and represents hydrogen, fluorine, chlorine, bromine, nitrile, $C_1-C_6$-alkyl, $C_1-C_6$-alkoxy, $C_1-C_6$-alkyl-thio, $C_1-C_6$-alkylsulphonyl, $C_1-C_4$fluoroalkyl. fluoro-$C_1-C_6$-alkoxy, fluoro-$C_1-C_6$-alkylthio or fluoro-$C_1-C_6$-alkylsulphonyl, or R[1] and R[2] together represent -O-X-O-, in which X denotes a fluorinated $C_1-C_2$-alkylene radical, with the proviso that R[1] does not represent 5-$CF_3$ if R[2] denotes hydrogen.

The substituents R[1] and R[2] are preferably located —if n=m=1—in the 4,6, the 5,6 or the 5,7 position.

The terms "fluoroalkyl", "fluoroalkoxy" and "fluoroalkylthio" do not exclude an additional substitution of these radicals by chlorine.

The term "fluoro-$C_1-C_6$-alkoxy" preferably encompasses difluoromethoxy, trifluoromethoxy, chlorodifluoromethoxy, 1,1,2,2-tetrafluoroethoxy, 2-chloro-1,1,2-trifluoroethoxy, pentafluoroethoxy and 1,1,2,3,3,3-hexafluoropropoxy.

The term "fluoro-$C_1-C_6$-alkylthio" preferably encompasses difluoromethylthio, trifluoromethylthio, chlorodifluoromethylthio, 1,1,2,2-tetrafluoroethylthio, 2-chloro-1,1,2trifluoroethylthio, pentafluoroethylthio and 1,1,2,3,3,3-hexafluoropropylthio.

The term "fluoro-$C_1-C_6$-alkylsulphonyl" preferably encompasses difluoromethylsulphonyl, trifluoromethylsulphonyl, chlorodifluoromethylsulphonyl, 1,1,2,2-tetrafluoroethylsulphonyl, 2-chloro-1,1,2-trifluoroethylsulphonyl, pentafluoroethylsulphonyl and 1,1,2,3,3,3-hexafluoropropylsulphonyl.

The term "substituted $C_2-C_{12}$-phenyl" preferably encompasses 2-chloro-4-trifluoromethyl-phenyl, 2,6-dichloro-4-trifluoromethyl-phenyl, 2-fluoro-4-trifluoromethylphenyl, 2-chloro-6-fluoro-4-trifluoromethyl-phenyl, 2-chloro-4-cyano-phenyl and 2,6-dichloro-4-cyano-phenyl.

The term "substituted $C_6-C_{12}$-phenoxy" preferably encompasses 2-chloro-4-trifluoromethyl-phenoxy, 2,6-dichloro-4-trifluoromethyl-phenoxy, 2-fluoro-4-trifluoromethyl-phenoxy, 2-chloro-6-fluoro-4-trifluoromethyl-phenoxy, 2-chloro-4-cyano-phenoxy and 2,6-dichloro-4-cyano-phenoxy.

Preferred compounds I correspond to the formulae

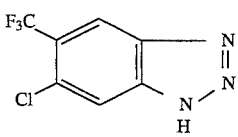
(II)

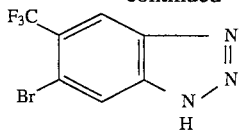
(III)

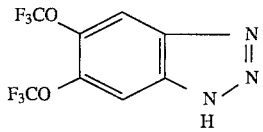
(IV)

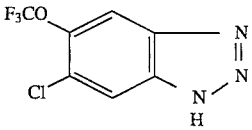
(V)

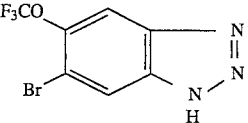
(VI)

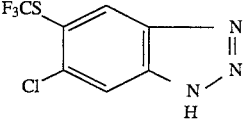
(VII)

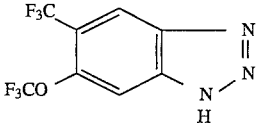
(VIII)

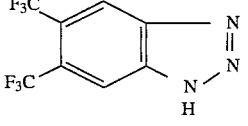
(IX)

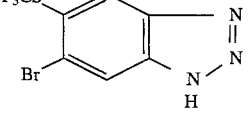
(X)

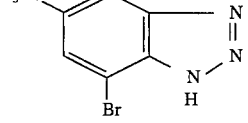
(XI)

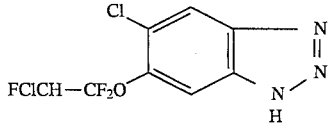
(XII)

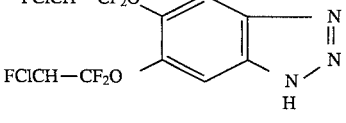
(XIII)

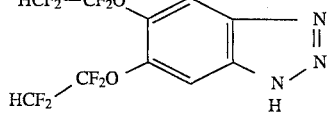
(XIV)

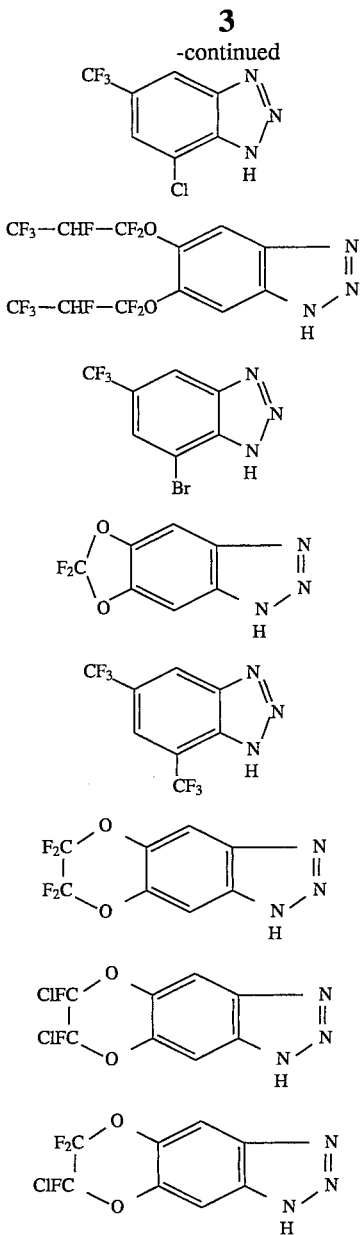

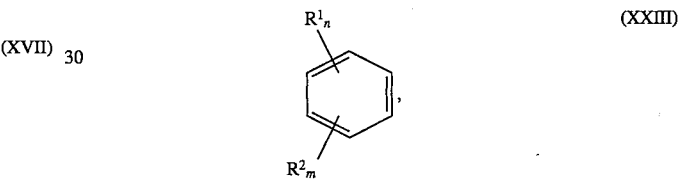

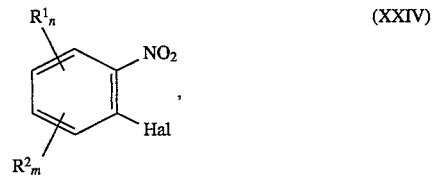

The fluorinated benzotriazoles according to the invention may be obtained by reacting the corresponding o-phenylenediamines with a nitrosating agent (e.g. sodium nitrite).

The condensation of the o-phenylenediamines with a nitrosating agent is preferably effected in solution. All solvents which are inert under the reaction conditions are, in principle, suitable as solvent or dispersant or diluent. Mixtures of solvents may also be used. Solvents which may be mentioned by way of example are: water, alcohols, ketones, organic acids, such as formic acid, acetic acid and propionic acid, DMF, toluene, chlorobenzene, dichloromethane, trichloroethylene, and the like.

Water in combination with an organic acid, for example, is advantageous since the reaction is carried out in the acid pH range.

However, the choice of the solvent/diluent also depends on the nature of the nitrosating agent. For example, if an alkali metal nitrite, such as sodium nitrite, is used, then this will be readily soluble in water, indicating this mode of implementation to be advantageous. In a similar manner, the method can also be carried out in other solvents using other nitrosating agents, such as methyl nitrite or iso-amyl nitrite.

Further nitrosating agents are nitrogen oxides, nitrosylsulphuric acid or nitrosyl chloride.

The addition of the nitrosating agent is preferably effected at a low temperature, that is at 0° to 10° C., but can also be carried out at temperatures below or above this. It is likewise possible to complete the reaction at an elevated temperature. For this purpose, a temperature range from 40° to 100° C. proved to be advantageous.

In order to obtain a product which is as pure as possible, the nitrosating agent is employed in molar equivalents or in a slight excess. In this way, complete reaction is achieved and separation of starting material and product is dispensed with. A larger excess of nitrosating agent does not interfere with the reaction and can be readily separated off, owing to the great difference in solubility. It favours the working up of the sample if a reaction medium is collected in which the product is poorly soluble so that it can be separated off, for example by filtration.

The o-phenylenediamines which are suitable for use as starting materials can be prepared in a variety of ways, independently of the nature of the $R^1$ and $R^2$ radicals:

If o-phenylenediamines are to be prepared in which both $R^1$ and $R^2$ represent donor groups in the 4 and 5 positions, e.g. compounds in which $R^1$ represents polyfluoroalkoxy or polyfluoroalkylthio and $R^1$ and/or $R^2$ represents fluorine, chlorine, bromine, alkyl, alkoxy or bisfluoroalkylamino, a benzene derivative of the formula can then be dinitrated and the nitro groups subsequently reduced. The dinitration can be carried out, for example, using $HNO_3H_2SO_4$ mixtures, which can optionally also contain oleum, at temperatures from, for example, 0° to 100° C. The reduction can be carried out, for example, using iron in the presence of aqueous hydrochloric acid and ethanol at temperatures from, for example, 50° to 100° C., or catalytically using elemental hydrogen, e.g. 1 to 100 bar, and in the presence of catalysts containing metals or compounds of metals from the 8th subgroup of the periodic system, in particular nickel or palladium, at, for example, 25° to 100° C.

If o-phenylenediamines are to be prepared in which $R^1$ has the meaning stated in relation to formula (I) and is located in the 4 position and $R^2$ represents Cl or Br in the 5 position, for example, a nitrobenzene derivative of 5 the formula, in which Hal represents fluorine, chlorine or bromine, can then be reacted with ammonia, thereby exchanging the Hal group for an amino group, and the resulting nitroaniline can be reduced. The exchange of halogen for an amino group can, for example, be carried out using liquid ammonia in the presence of water and a tetraalkylammonium salt at temperatures from, for example, 80° to 200° C. in a pressure vessel. The nitroaniline can be reduced, for example, in analogy with the above-described reduction of dinitro compounds.

If o-phenylenediamines are to be prepared in which $R^1$ has the meaning stated in relation to formula (I) and is located in the 4 position and $R^2$ represents chlorine or bromine in the 6 position, for example, a nitroaniline of the formula

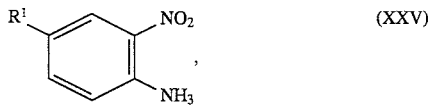

(XXV)

can then be reacted with a chlorinating or brominating agent, thereby introducing a chlorine or bromine atom into the meta position to the nitro group, and the nitro group can be subsequently reduced. Elemental chlorine and elemental bromine, and other customary chlorinating and brominating agents, are suitable chlorinating or brominating agents. Suitable solvents are, for example, water, dilute mineral acids, acetic acid, chloroalkanes and trifluoroacetic acid, and suitable temperatures are, for example, those from −20° to +50° C. The reduction can be effected, for example, in analogy with the above-described reduction of dinitro compounds.

o-Phenylenediamines which are substituted three or four times can be prepared in analogy with the above-described processes.

Most of the abovementioned o-phenylenediamines, and processes for their preparation, are described in German Patent Application P 42 37 564.9 and in EP-A 251 013.

The fluorinated benzotriazoles according to the invention are valuable intermediates for preparing active compounds for pharmaceuticals and plant-protection agents.

The compounds of the formula (I) according to the invention also themselves exhibit a strong effect against pests and can be employed in practice for combating unwanted pernicious organisms. The active compounds are suitable for use as plant-protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation:

Pythium species, such as, for example, *Pythium ultimum*;
  Phytophthora species, such as, for example, *Phytophthora infestans*;
Pseudoperonospora species, such as, for example, *Pseudoperonospora humuli* or *Pseudoperonospora cubenis*;
Plasmopara species, such as, for example, *Plasmopara viticola*;
Peronospora species, such as, for example, *Peronospora pisi* or *P. brassicae*;
Erysiphe species, such as, for example, *Erysiphe graminis*;
Sphaerotheca species, such as, for example, *Sphaerotheca fuliginea*;
Podosphaera species, such as, for example, *Podosphaera leucotricha*;
Venturia species, such as, for example, *Venturia inaequalis*;
Pyrenophora species, such as, for example, *Pyrenophora teres* or *P. graminea* (conidia form: Drechslera, syn: Helminthosporium);
Cochliobolus species, such as, for example, *Cochliobolus sativus* (conidia form: Drechslera, syn: Helminthosporium);

Uromyces species, such as, for example, *Uromyces appendiculatus*;
Puccinia species, such as, for example, *Puccinia recondita*;
Tilletia species, such as, for example, *Tilletia caries*;
Ustilago species, such as, for example, *Ustilago nuda* or *Ustilago avenae*;
Pellicularia species, such as, for example, *Pellicularia sasakii*;
Pyricularia species, such as, for example, *Pyricularia oryzae*;
Fusarium species, such as, for example, *Fusarium culmorum*;
Botrytis species, such as, for example, *Botrytis cinerea*;
Septoria species, such as, for example, *Septoria nodorum*;
Leptosphaeria species, such as, for example, *Leptosphaeria nodorum*;
Cercospora species, such as, for example, *Cercospora canescens*;
Alternaria species, such as, for example, *Alternaria brassicae* and
Pseudocercosporella species, such as, for example, *Pseudocercosporella herpotrichoides*.

The good toleration, by plants, of the active compounds, at the concentrations required for combating plant diseases, permits treatment of above-ground parts of plants, of vegetative propagation stock and seeds, and of the soil.

In this context, the active compounds according to the invention may be employed particularly successfully for combatting Phytophthora on tomatoes and Venturia species on apples.

Depending on their particular physical and/or chemical properties, the active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and furthermore in formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite and diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyethylene fatty alcohol ethers, for example alkylaryl polyglycol ethers, alkylsulphonates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain 0.0000001 to 95% by weight of active compound, preferably 0.0001 to 90% by weight.

The active compounds according to the invention can be present in the formulations as a mixture with other known active compounds, such as fungicides, insecticides, acaricides and herbicides, as well as in mixtures with fertilizers[1] and growth regulators.

The active compounds can be used as such or in the form of their formulations or the use forms prepared therefrom, such as ready-to-use solutions, suspensions, wettable powders, pastes, soluble powders, dusting agents and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can vary within a substantial range. They are, in general, between 1 and 0.0001% by weight, preferably between 0.5 and 0.0001% by weight.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

EXAMPLES

Preparation of starting materials (o-phenylenediamines) for the novel benzotriazoles a) 320 g of 1,2-bis-(2-chloro-1,1,2-trifluoroethoxy)benzene were added dropwise to 500 g of a mixed acid containing 33% by weight of $HNO_3$ and 67% by weight of $H_2SO_4$. After one hour at 40° C., 250 ml of 20% strength by weight oleum were added dropwise. Subsequently, the mixture was heated to 80° C. and then stirred for 15 hours. A further 120 ml of 20% strength by weight oleum and 250 g of the above-mentioned mixed acid were then added dropwise. After 6 hours at 80° to 82° C., the mixture was cooled down and poured onto ice. The organic phase was separated off and washed with water. Following azeotropic drying with 1,2-dichloroethane, 350 g of 1,2-di-nitro- 4,5-bis-(2-chloro-1,1,2-trifluoroethoxy)benzene were obtained, which was 98% pure by weight (oil, $N_D^{20}$: 1.4832, GC 99.1%).

350 g of this dinitro compound were added dropwise to a mixture consisting of 1.5 l of ethanol, 50 ml of water, 30 ml of concentrated aqueous hydrochloric acid and 470 g of iron filings, and this new mixture then heated to boiling at reflux for a total of 15 hours. Subsequently, the cooled solution was filtered and concentrated, and the residue was recrystallized from cyclohexane. 216 g of 1,2-diamino-4,5 bis-(2-chloro-1,1,2-trifluoroethoxy)-benzene were obtained with a melting point of 58° to 60° C.

b) 24 g of finely powdered 2-nitro-4-trifluoromethylmercapto-aniline were dissolved in 50 ml of trifluoroacetic acid, and 18 g of bromine were metered in at 20° C. The mixture was then stirred at 20° C. for 3 hours and subsequently at 40° C. for a further 30 minutes, after which it was poured onto water and the product was taken up in dichloromethane. 31 g of 6-bromo-2-nitro-4-trifluoromethylmercapto-aniline resulted after removing the solvent.

155 g of the nitroaniline prepared in this way were heated to boiling at reflux for 15 hours in 700 ml of ethanol together with 15 ml of water, 10 ml of concentrated aqueous hydrochloric acid and 70 g of iron filings, and the mixture was then filtered; the filtrate was freed of solvent under reduced pressure and the solid crude product was recrystallized from cyclohexane. 112 g of 6-bromo-4-trifluoromethyl-mercapto-1,2-diamino-benzene were obtained with a melting point of 60° to 61° C.

The remaining o-phenylenediamines which are required for preparing the benzotriazoles according to the invention may be prepared in an analogous manner.

Benzotriazole XVI

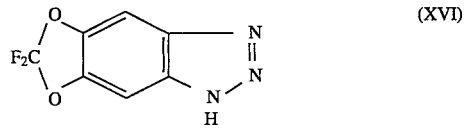

10 g of diamine of the formula

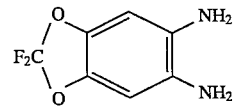

were added to a mixture consisting of 75 ml of water and 6 ml of glacial acetic acid and the whole mixture was then stirred for 30 minutes. After cooling the mixture down to 0° C., 8 g of sodium nitrite, dissolved in 25 ml of water, were rapidly added dropwise. Subsequently, the mixture was stirred at 0° to 5° C. for 1 hour and then at 80° C. for 3 hours. After cooling down to room temperature, the solid material was filtered off with suction and then washed with a little water. After drying, 9.6 g of the desired product were obtained with a melting point of 203° to 204° C.

The following were obtained in an analogous manner:

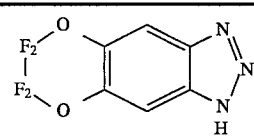 m.p.: 147–148° C.

9
-continued

| Structure | m.p. |
|---|---|
| ClFCH₂-/ClFCH₂- benzotriazole | m.p. 151–152° C. |
| CF₃-/Cl- benzotriazole | m.p.: 159–160° C. |
| CF₃-/Br- benzotriazole | m.p.: 167–168° C. |
| CF₃S-/Br- benzotriazole | m.p.: 228–229° C. |
| Cl-/Cl₂CH—CF₂O- benzotriazole | m.p.: 159–160° C. |
| Cl—CHF—CF₂O-/Cl—CHF—CF₂O- benzotriazole | m.p.: 153–154° C. |
| CF₃O- benzotriazole | m.p.: 107–109° C. |
| HCF₂CF₂O- benzotriazole | m.p.: 77–78° C. |
| CF₃O-/Cl- benzotriazole | m.p.: 124–125° C. |
| CF₃S- benzotriazole | m.p.: 125–127° C. |

Application

Venturia test (apple)/protective
Solvent: 12.5 parts by weight of acetone
Emulsifier: 0.3 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (Venturia inaequalis) and then remain in an incubation cabin at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, a clearly superior activity compared with the prior art is shown, for example, by the compounds according to the following preparation examples:

TABLE

| | Venturia test (apple)/protective |
|---|---|
| Active compound | Efficacy in % of the untreated control at an active compound concentration of 0.025% by weight |
| F₂C(O)(O)-benzotriazole NH | 100 |
| Br-/F₃C—S- benzotriazole NH | 78 |
| F₃C-/Cl- benzotriazole NH | 89 |
| F₂C(O)/F₂C(O)- benzotriazole NH | 89 |

We claim:

1. A benzotriazole which contains at least two fluorine atoms per molecule and corresponds to the formula

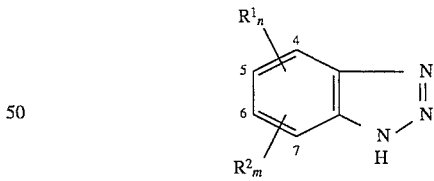

in which n and m=1 or 2,

R¹ represents fluoro-$C_1$–$C_6$-alkoxy or fluoro-$C_1$–$C_6$-alkylthio, and

R² represents hydrogen, fluorine, chlorine, bromine, nitrile, $C_1$–$C_6$-alkyl, $C_1$–$C_6$-alkoxy, $C_1$–$C_6$-alkylthio, $C_1$–$C_6$-akylsulphonyl, $C_1$–$C_4$-fluoroalkyl, fluoro-$C_1$–$C_6$-alkoxy, fluoro-$C_1$–$C_6$-alkylthio or fluoro-$C_1$–$C_6$-alkylsulphonyl, or R¹ and R² together represent O-X-O-, in which X denotes a fluorinated $C_1$–$C_2$-alkenylene radical.

2. A compound according to claim 1, wherein the compounds are

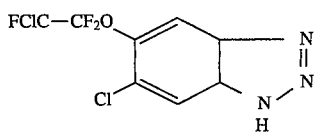
or
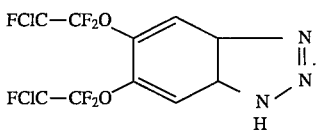
3. A benzotriazole according to claim 1, wherein $R^1$ and $R^2$ together represent -O-X-O-, in which X denotes a fluorinated $C_1$–$C_2$-alkylene radial.
4. A compound according to claim 1, wherein the compounds are
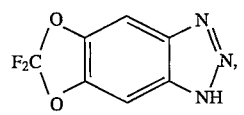
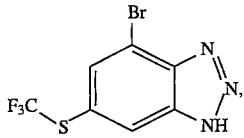
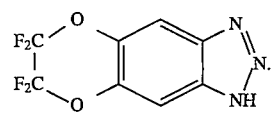
* * * * *